United States Patent [19]

Wehinger et al.

[11] 4,166,855

[45] Sep. 4, 1979

[54] 1,4-DIHYDRO-2,6-DIMETHYL-4-(3-NITROPHENYL)-3,5-PYRIDINEDICARBOXYLIC ACID ESTER, AND ITS USE AS A PERIPHERAL VASODILATOR

[75] Inventors: Egbert Wehinger, Velbert; Friedrich Bossert, Wuppertal; Horst Meyer, Wuppertal; Arend Heise, Wuppertal; Stanislav Kazda, Wuppertal; Kurt Stoepel, Wuppertal; Wulf Vater, Leverkusen, all of Fed. Rep. of Germany

[73] Assignee: Bayer Aktiengesellschaft, Leverkusen, Fed. Rep. of Germany

[21] Appl. No.: 840,065

[22] Filed: Oct. 6, 1977

[30] Foreign Application Priority Data

Oct. 30, 1976 [DE] Fed. Rep. of Germany ....... 2650013

[51] Int. Cl.$^2$ .................... C07D 213/55; A61K 31/44
[52] U.S. Cl. ...................................... 424/266; 546/321
[58] Field of Search ................. 260/295.5 R; 424/266; 546/321

[56] References Cited

U.S. PATENT DOCUMENTS 3,799,934  3/1974  Meyer et al. ................. 260/294.8 G

*Primary Examiner*—Alan L. Rotman
*Attorney, Agent, or Firm*—Sprung, Felfe, Horn, Lynch & Kramer

[57] ABSTRACT

The invention provides a novel compound, 1,4-dihydro-2,6-dimethyl-4-(3-nitrophenyl)-3,5-pyridinedicarboxylic acid isopropyl 2-propoxyethyl ester and processes for its preparation. In addition, the invention includes the provision of compositions containing the compound of the invention and methods for treating warm-blooded animals for peripheral perfusion disturbances.

9 Claims, No Drawings

1,4-DIHYDRO-2,6-DIMETHYL-4-(3-NITRO-PHENYL)-3,5-PYRIDINEDICARBOXYLIC ACID ESTER, AND ITS USE AS A PERIPHERAL VASODILATOR

The present invention relates to 1,4-dihydro-2,6-dimethyl-4-(3-nitrophenyl)-3,5-pyridinedicarboxylic acid isopropyl 2-propoxyethyl ester, which is new, several processes for its preparation and its use as a peripheral vasodilator.

It has already been disclosed that 1,4-dihydro-2,6-dimethyl-4-phenyl-3,5-pyridine-dicarboxylic acid diethyl ester is obtained when benzylideneacetoaceic acid ethyl ester is reacted with β-aminocrotonic acid ethyl ester or acetoacetic acid ethyl ester and ammonia (E. Knoevenagel, Ber. dtsch. chem. Ges. 31, 743 (1898)). Moreover, it is known that certain 1,4-dihydropyridines have interesting pharmacological properties (F. Bossert and W. Vater, Naturwissenschaften 58, 578 (1971)).

Furthermore, it has been disclosed in the earlier German Offenlegungsschriften (German Published Specifications) Nos. 2,117,571 and 2,117,573 of the applicant, that similar dihydropyridines can be used as coronary agents.

The present invention provides 1,4-dihydro-2,6-dimethyl-4-(3-nitrophenyl)-3,5-pyridinedicarboxylic acid isopropyl 2-propoxy-ethyl ester of the formula I

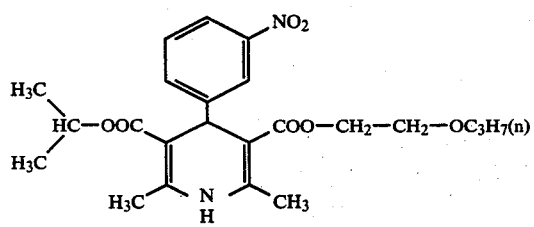

The compound of the invention has a very strong and long-lasting peripherally-vasodilating action which was not to be expected from the state of the art.

It has also been found that the new active compound of the formula I is obtained when (A) 3'-nitrobenzylideneacetoacetic acid isopropyl ester (formula II)

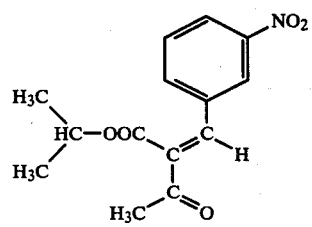

is reacted with β-aminocrotonic acid 2-propoxyethyl ester (formula III)

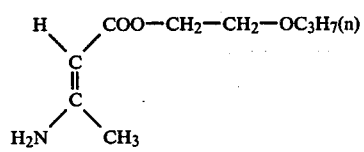

as such or in the presence of water and/or inert organic solvents, or (B) 3'-nitrobenzylideneacetoacetic acid isopropyl ester (formula II) is reacted with acetoacetic acid 2-propoxyethyl ester (formula IV)

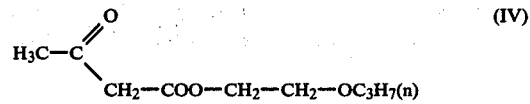

and ammonia, as such or in the presence of water and/or inert organic solvents, or (C) 3'-nitrobenzylideneacetoacetic acid 2-propoxyethyl ester (formula V)

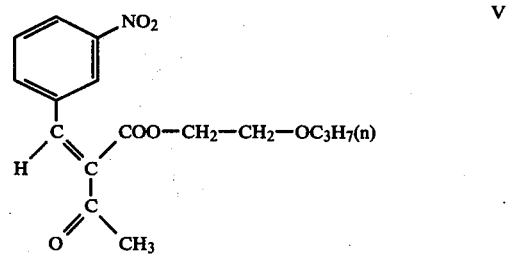

is reacted with β-aminocrotonic acid isopropyl ester (formula VI)

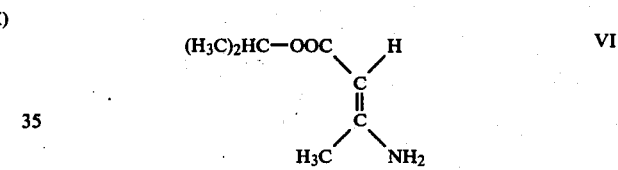

as such or in the presence of water and/or inert organic solvents, or (D) 3'-nitrobenzylideneacetoacetic acid 2-propoxyethyl ester (formula V) is reacted with acetoacetic acid isopropyl ester (formula VII)

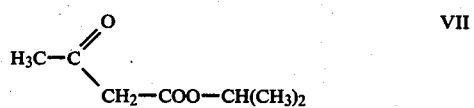

and ammonia, as such or in the presence of water and/or inert organic solvents, or (E) β-aminocrotonic acid isopropyl ester (formula VI) is reacted with 3-nitrobenzaldehyde (formula VIII)

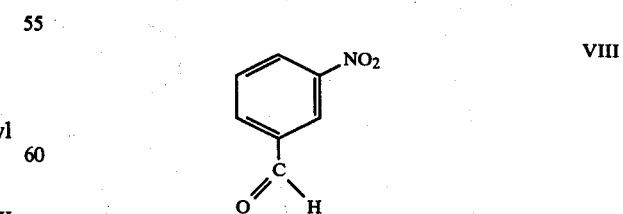

and with acetoacetic acid 2-propoxyethyl ester (formula IV), as such or in the presence of water and/or inert organic solvents, or (F) β-aminocrotonic acid 2-propoxyethyl ester (formula III), 3-nitrobenzaldehyde (formula VIII) and acetoacetic acid isopropyl ester (formula VII) are reacted with one another as such or in the presence of water and/or inert organic solvents.

Surprisingly, the compound according to the invention, of the formula I has a particularly strong peripheral vasodilating action.

The compound according to the invention is chiral and can exist in stereoisomeric forms which behave as mirror images (enantiomers, antipodes). These can in turn again occur in various conformations. The present invention includes the compound of the invention in both the racemic form and the antipodes.

Depending of the nature of the starting materials used, the synthesis of the compound according to the invention can be represented by the following equations:

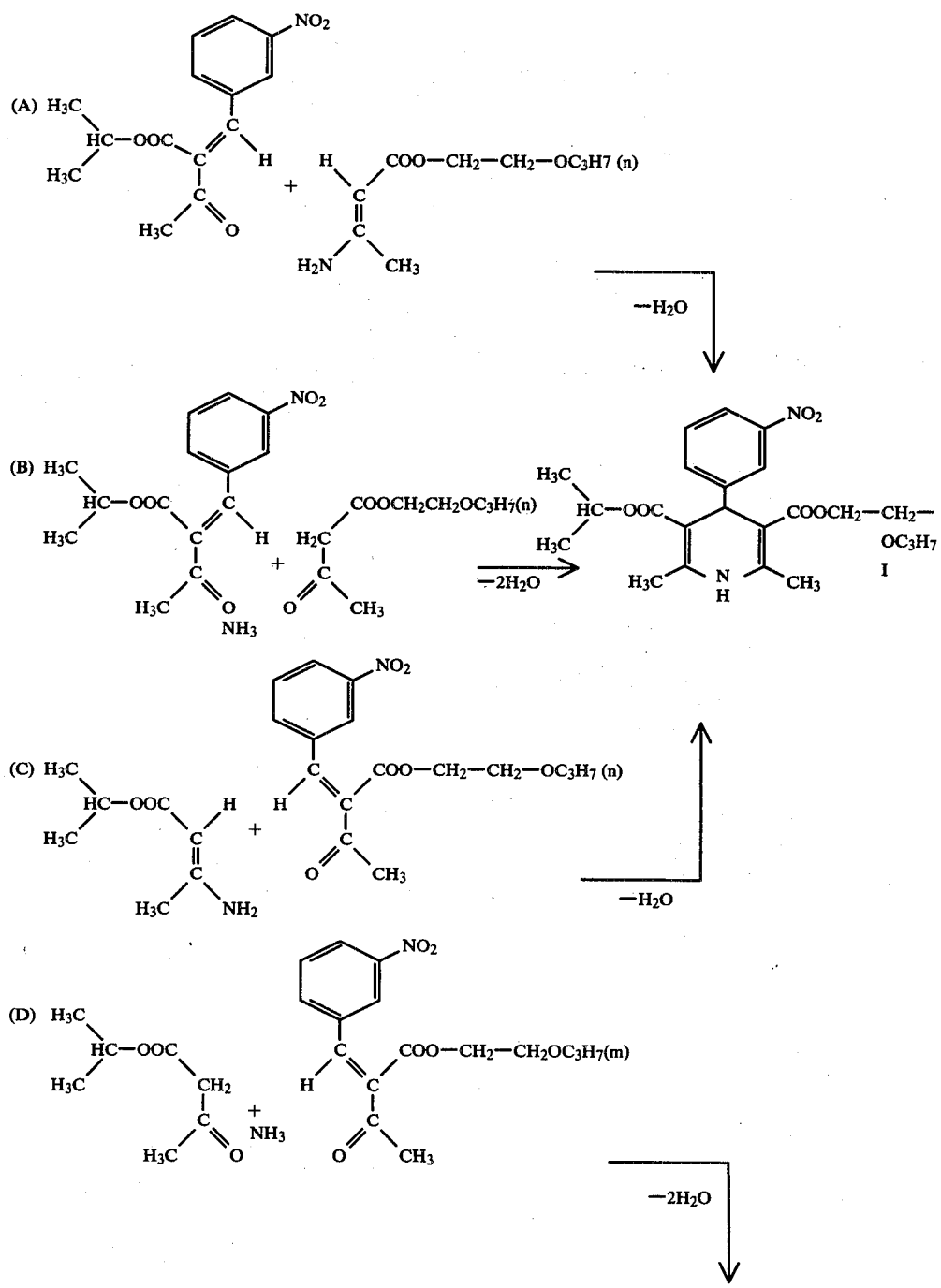

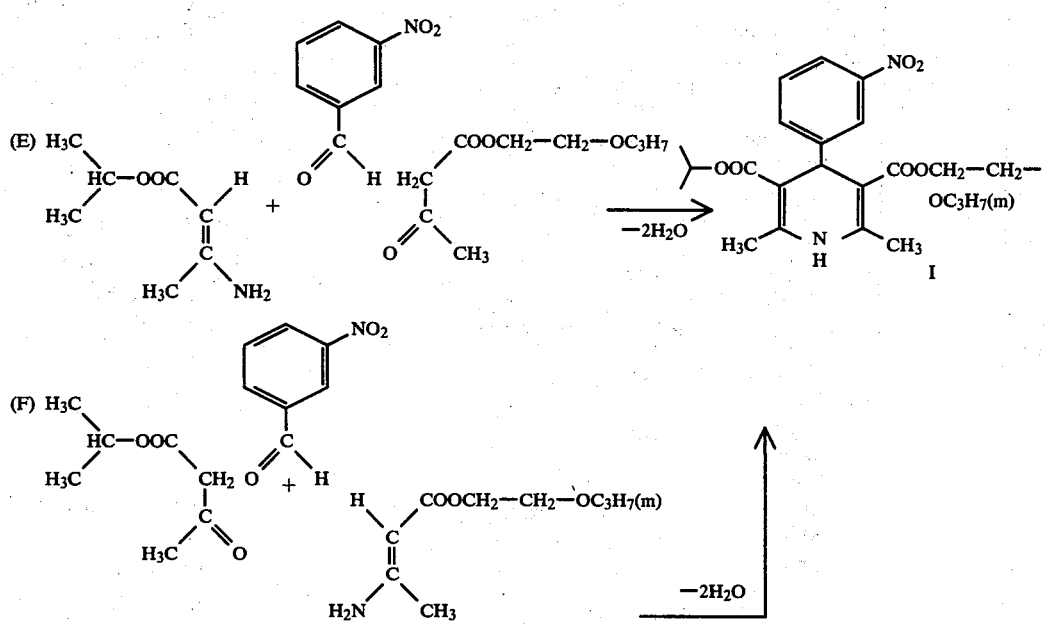

The substances of the formula II to VIII used as starting materials are known from the literature or can be prepared by methods which are known from the literature (see, for example, G. Jones "The Knoevenagel Condensation" in Org. Reactions, volume XV, 204 et seq. (1967); A.C. Cope, J. Amer. chem. Soc. 67, 1,017 (1945); and D. Borrmann, "Umsetzung von Diketen mit Alkoholen, Phenolen und Mercaptanen" ("The Reaction of Diketene with Alcohols, Phenols and Mercaptans") in Houben-Weyl, Methoden der Organischen Chemie (Methods of Organic Chemistry) volume VII/4, et seq. (1968)).

In carrying out the processes A–F according to the invention, the substances participating in the reaction are each preferably employed in approximately equimolar amounts. The ammonia used is appropriately added in excess.

Diluents which can be used are water and all inert organic solvents. These include, preferably, alcohols, such as alkanols, having 1 to 4 carbon atoms, i.e. methanol or propanol, or ethers, such as dialkyl ethers having up to 8 carbon atoms, i.e. diethyl ether, tetrahydrofurane or dioxane, or glacial acetic acid, pyridine, dimethylformamide, dimethylsulphoxide, acetonitrile or hexamethylphosphoric acid triamide.

The reaction temperatures can be varied within a relatively wide range. In general, the reaction is carried out between about 20° and 200° C., preferably at about 50° to 120° C., or in particular at the boiling point of the particular solvent.

The reaction can be carried out under normal pressure, but also under increased pressure. In general, it is carried out under normal pressure.

The above preparative processes are only given for illustration and the preparation of compound I is not limited to these processes, but any modification of these processes can be used in a similar manner for the preparation of compound I.

The compound according to the invention is a substance which can be used as a medicament. It effects a strong and long-lasting peripheral vasodilation on enteral and parenteral administration and can thus be employed for the therapy and prophylaxis of peripheral perfusion disturbances.

The present invention includes a pharmaceutical composition containing as active ingredient the compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient the compound of the invention in the form of a sterile or isotonic aqueous solution.

The invention also provides a medicament in dosage unit form comprising the compound of the invention.

The invention also provides a medicament in the form of tablets (including lozenges and granules), dragees, capsules, pills, ampoules or suppositories comprising the compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions are emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 90% of the active ingredient by weight of the total composition.

In addition to the compound of the invention, the pharmaceutical compositions and medicaments according to the invention can also contain other pharmaceutically active compounds.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 0.0005 g to 0.5 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably perorally or intravenously. Preferred pharmaceutical compositions and medicaments are therefore those adapted for oral or intravenous administration.

In general, it has proved advantageous, in the case of intravenous administration, to administer amounts of about 0.0001 to 1 mg/kg, preferably about 0.0014 to 0.10 mg/kg, of body weight daily to achieve effective results, and in the case of enteral administration the dosage is about 0.01 to 10 mg/kg, preferably 0.1 to 1.0 mg/kg, of body weight daily.

Nevertheless, it can at times be necessary to deviate from the amounts given, and in particular to do so as a function of the body weight of the test animal or of the nature of the administration route, but also because of the species of animal and its individual behaviour towards the medicament or because of the time at which administration takes place.

Thus, it may be sufficient, in some cases, to manage with less than the abovementioned minimum amount, whilst in other cases the upper limit mentioned must be exceeded. Where relatively large amounts are administered it can be advisable to divide these into several individual administrations over the course of the day. The same dosage range is envisaged for administration in human medicine.

PREPARATION EXAMPLES 1,4-Dihydro-2,6-dimethyl-4-(3-nitrophenyl)-3,5-pyridinedicarboxylic acid isopropyl 2-propoxyethyl ester

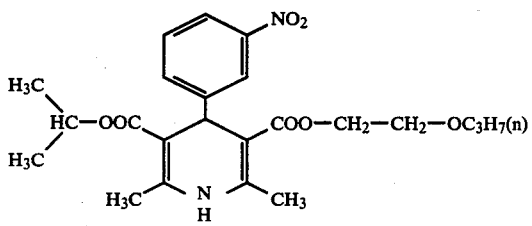

(A) 27.7 g (0.1 mol) of 3'-nitrobenzylideneacetoacetic acid isopropyl ester were heated under reflux, together with 18.7 g (0.1 mol) of β-aminocrotonic acid 2-propoxyethyl ester, in 160 ml of ethanol for 20 hours in a nitrogen atmosphere. After the reaction mixture had cooled, the solvent was distilled off in vacuo and the oily residue was taken up in 50 ml of an ether/ethanol mixture (2:1). The crude product crystallised out after some time and was filtered off and recrystallised from ethanol.

Melting point: 87°–89° C., yield: 29 g (65%).

(B) 27.7 g (0.1 mol) of 3'-nitrobenzylideneacetoacetic acid isopropyl ester were heated under reflux, together with 18.8 g (0.1 mol) of acetoacetic acid 2-propoxyethyl ester and 12 g (0.18 mol) of a 25 percent strength aqueous ammonia solution, in 160 ml of isopropanol for 24 hours in a nitrogen atmosphere. The solvent was then distilled off in vacuo and the oily residue was mixed thoroughly with a little ethanol. After seeding with an authentic sample, the crude product solidified. It was filtered off and recrystallised from ethanol.

Melting point: 86°–88° C., yield: 21 g (47%).

(C) 32.1 g (0.1 mol) of 3'-nitrobenzylideneacetoacetic acid 2-propoxyethyl ester were heated under reflux, together with 14.3 g (0.1 mol) of β-aminocrotonic acid isopropyl ester, in 160 ml of ethanol for 20 hours in a nitrogen atmosphere. The solvent was then distilled off in vacuo and 50 ml of an ether/ethanol mixture (2:1) were added to the oily residue. The crude product crystallised out after some time and was filtered off and recrystallised from ethanol.

Melting point: 86°–88° C., yield: 27 g (60.5%).

(D) 32.1 g (0.1 mol) of 3'-nitrobenzylideneacetoacetic acid 2-propoxyethyl ester were heated under reflux, together with 14.4 g (0.1 mol) of acetoacetic acid isopropyl ester and 12 g (0.18 mol) of a 25 percent strength aqueous ammonia solution, in 160 ml of isopropanol for 24 hours in a nitrogen atmosphere. After the reaction mixture had cooled, the solvent was distilled off in vacuo and the oily residue was mixed thoroughly with a little ethanol and seeded with a small authentic sample. The product crystallised completely and was filtered off and recrystallised from ethanol.

Melting point: 86°–88° C., yield: 18 g (40%).

(E) 14.3 g (0.1 mol) of β-aminocrotonic acid isopropyl ester were heated under reflux, together with 15.1 g (0.1 mol) of 3-nitrobenzaldehyde and 18.8 g (0.1 mol) of acetoacetic acid 2-propoxyethyl ester, in 160 ml of dioxane for 24 hours in a nitrogen atmosphere. The solvent was then distilled off in vacuo and the oily residue was seeded with an authentic sample. The product crystallised completely and was taken up in a little ether, filtered off and recrystallised from ethanol.

Melting point: 86°–88° C., yield: 26 g (58%).

(F) 18.7 g (0.1 mol) of β-aminocrotonic acid 2-propoxyethyl ester were heated under reflux, together with 15.1 g (0.1 mol) of 3-nitrobenzaldehyde and 14.4 g (0.1 mol) of acetoacetic acid isopropyl ester in 160 ml of isopropanol for 24 hours in a nitrogen atmosphere. After the reaction mixture had cooled, the solvent was distilled off in vacuo and the oily residue was mixed thoroughly with a little ethanol and seeded with a small authentic sample. The product crystallised completely and was filtered off and recrystallised from ethanol.

Melting point: 86°–88° C., yield: 22 g (49%).

What we claim is:

1. 1,4-Dihydro-2,6-dimethyl-4-(3-nitrophenyl)-3,5-pyridinedicarboxylic acid isopropyl 2-propoxyethyl ester of the formula I

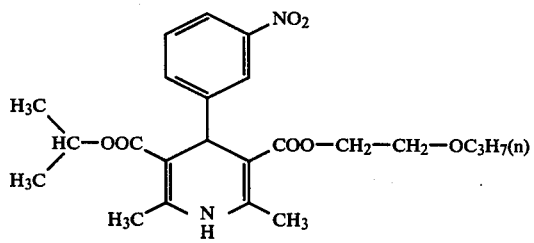

2. A pharmaceutical composition containing as an active ingredient an effective amount as a peripheral vasodilator of the compound of claim 1 in admixture with a solid or liquefied gaseous diluent or in admixture with a liquid diluent other than a solvent of a molecular weight less than 200 except in the presence of a surface-active agent.

3. A pharmaceutical composition containing as an active ingredient an effective amount as a peripheral vasodilator of the compound of claim 1 in the form of a sterile isotonic aqueous solution.

4. A composition according to claim 3 contaning from 0.5 to 90% by weight of the said active ingredient.

5. A medicament in dosage unit form comprising an effective amount as a peripheral vasodilator of a compound of claim 1 together with an inert pharmaceutical diluent.

6. A medicament of claim 5 in the form of tablets, pills, dragees, capsules, ampoules, or suppositories.

7. A method of combating peripheral perfusion disturbances in warm-blooded animals in need of such treatment which comprises administering to the animals an effective amount of the compound of claim 1 either alone or in admixture with a inert diluent or in the form of a medicament.

8. A method according to claim 7 in which the active compound is administered in an amount of from 0.0001 to 10% mg per kg body weight per day.

9. A method according to claim 8 in which the active compound is administered orally or intravenously.

* * * * *